US00PP10248P

United States Patent [19]

van Rijn

[11] Patent Number: Plant 10,248

[45] Date of Patent: Feb. 17, 1998

[54] ANTHURIUM PLANT NAMED 'LAURA'

[75] Inventor: Magdalena J. M. van Rijn, Schipluiden, Netherlands

[73] Assignee: Rijnplant, Schipluiden, Netherlands

[21] Appl. No.: 761,286

[22] Filed: Dec. 6, 1996

[51] Int. Cl.[6] ..... A01H 5/00

[52] U.S. Cl. ..... Plt./88.1

[58] Field of Search ..... Plt./88.1

*Primary Examiner*—James R. Feyrer
*Assistant Examiner*—Elizabeth C. Kemmerer
*Attorney, Agent, or Firm*—C. A. Whealy

[57] ABSTRACT

A distinct cultivar of Anthurium plant named 'Laura', characterized by its large plant size; upright and vigorous growth habit; large dark green leaves that are glossy and ovate to cordate in shape; numerous flowers that are positioned above the foliage on strong and erect peduncles; large shiny red spathes; and good post-production longevity.

2 Drawing Sheets

The present invention relates to a new and distinct cultivar of Anthurium plant, botanically known as *Anthurium andreanum*, and hereinafter referred to by the cultivar name Laura.

The new cultivar is a product of a planned breeding program conducted by the inventor in Schipluiden, The Netherlands. The new cultivar originated from a cross by the inventor between the proprietary *Anthurium andreanum* selection RP 3 as the female or seed parent and the proprietary *Anthurium andreanum* selection RP 6 as the male or pollen parent. The cultivar Laura was discovered and selected by the inventor as a plant within the progeny of the stated cross in a controlled environment in Schipluiden, The Netherlands.

Asexual propagation of the new cultivar by tissue culture at Schipluiden, The Netherlands, has shown that the unique features of this new Anthurium plant are stable and reproduced true to type in successive generations of asexual propagation.

The new Anthurium has not been observed under all possible environmental conditions. The phenotype may vary somewhat with variations in environment such as temperature and light intensity, without, however, any variance in genotype. The following observations, measurements and comparisons describe plants grown in Schipluiden, The Netherlands, in a glass greenhouse with an average day temperature of 25C. and an average night temperature of 19C.

The following traits have been repeatedly observed and are determined to be the unique characteristics of 'Laura'. These characteristics in combination distinguish 'Laura' as a new and distinct cultivar:

1. Relatively large plants that are upright and vigorous in growth habit.
2. Large dark green leaves that are glossy and ovate to cordate in shape.
3. Numerous flowers that are positioned above the foliage on strong and erect peduncles.
4. Large shiny red spathes.
5. Good post-production longevity.

The new Anthurium can be compared to its seed parent cultivar, the proprietary selection RP 3. In addition to spathe color, the new cultivar is different from plants of RP 3 in the following characteristics:

1. Plants of the cultivar 'Laura' have a more triangular leaf shape than plants of the selection RP 3.
2. Leaves of plants of the cultivar 'Laura' are darker in color than leaves of plants of the selection RP 3.
3. The rooting habit of plants of the cultivar 'Laura' is better than plants of the selection RP 3.

The new Anthurium can be compared to its pollen parent cultivar, the selection RP 6. In addition to spathe color, the new cultivar is different from plants of RP 6 in the following characteristics:

1. Plants of the cultivar 'Laura' are not as freely branching as plants of the selection RP 6.
2. Plants of the cultivar 'Laura' have darker and larger leaves than plants of the selection RP 6.
3. Plants of the cultivar 'Laura' have larger flowers than plants of the selection RP 6.
4. Plants of the cultivar 'Laura' flower later than plants of the selection RP 6.

The new Anthurium is similar to the cultivar 'Leny' (U.S. Plant patent filed concurrently with this application). The new Anthurium differs from the cultivar 'Leny' in the following characteristics:

1. Plants of the cultivar 'Laura' are larger than plants of the cultivar 'Leny'.
2. Plants of the cultivar 'Laura' have larger leaves than plants of the cultivar 'Leny'.
3. Plants of the cultivar 'Laura' have larger and broader spathes and longer spadices than plants of the cultivar 'Leny'. 4. Plants of the cultivar 'Laura' have spadices with a pink apex whereas plants of the cultivar 'Leny' have spadices with a yellow apex.
5. Plants of the cultivar 'Laura' have longer peduncles than plants of the cultivar 'Leny'.

The accompanying colored photographs illustrate the overall appearance of the new cultivar, showing the colors as true as it is reasonably possible to obtain in colored reproductions of this type.

The first photograph comprises a top perspective view of a typical potted plant of 'Laura'.

The second photograph comprises a close-up view of typical flowers of 'Laura'.

In the following description, color references are made to The Royal Horticultural Society Colour Chart except where general terms of ordinary dictionary significance are used.

Botanical classification: *Anthurium andreanum* cultivar 'Laura'.

Parentage:

*Seed or female parent.*—Inventor's proprietary *Anthurium andreanum* selection RP 3.

*Pollen or male parent.*—Inventor's proprietary *Anthurium andreanum* selection RP 6.

Propagation: By tissue culture.

Plant description:

*Plant shape.*—Upright, inverted triangle, symmetrical.

*Growth habit.*—Erect when young, becoming outwardly arching as leaves develop. Moderate branching. Appropriate for 17 to 70-cm containers.

*Plant height.*—45 to 60 cm from soil level to top of leaf plane.

*Plant vigor.*—High.

*Growth rate.*—Rapid.

*Crop time.*—About 16 to 17 months are usually required from planting of a young plant to a finished plant with a height of 65 to 70 cm.

*Rooting habit.*—Freely branching, numerous fleshy roots.

*Foliage description.*—Quantity of leaves per finished plant: About 50. Leaf shape: Ovate to cordate. Leaf apex: Apiculate. Leaf base: Cordate. Margin: Entire. Leaf texture: Leathery, smooth, glabrous, glossy. Leaf size: Length: 17 to 22 cm. Width: 13 to 17 cm. Leaf color: Young, abaxial surface: Darker than 144A. Young, adaxial surface: 146C. Mature, abaxial surface: Between 139A and 147A. Mature, adaxial surface: Darker than 144A. Venation, abaxial surface: Lighter green than surrounding tissue. Venation, adaxial surface: Darker green than surrounding tissue. Petiole length, primary shoot: About 26 cm. Petiole color: 145A.

Flower description:

*Flower arrangement.*—Spathe with spadix held clearly above the foliage. Flowers arise from leaf axils.

*Flower longevity.*—Flowers last about 6 weeks under winter conditions and up to 3 months under summer conditions. Flowers persistent.

*Quantity of flowers per spadix.*—150 to 200.

*Flower shape.*—Rounded.

*Flower diameter.*—About 1 mm.

*Spathe.*—Appearance: Shiny. Shape: Broadly ovate. Apex: Mucronate. Base: Cordate. Margin: Entire. Texture: Shiny. Aspect: Flat to slightly curved upward at margins. Size: Length: 6 to 8 cm. Width: 8 to 11 cm. Color: When opening: 45A. Open flower, abaxial surface: 45A. Open flower, adaxial surface: 47B/47C. After senescence: Darker than 46A.

*Spadix.*—Cross section: Rounded to slightly elliptic. Longitudinal axis: Weakly recurved. Size: Length: 5 to 7 cm. Diameter: About 8 mm. Color: Base: Greenish. Mature: 38D. Apex: 39A/39B. After senescence: 146A.

*Peduncle.*—Aspect: Strong and erect. Length: 40 to 50 cm. Color 145A.

*Reproductive organs.*—Androecium: Pollen color: Cream white, 158D. Gynoecium: Stigma shape: Ovoid.

Disease resistance: No resistance to disease has been noted.

Seed development: Seed development is rarely observed.

It is claimed:

1. A new and distinct cultivar of Anthurium plant named 'Laura', as illustrated and described.

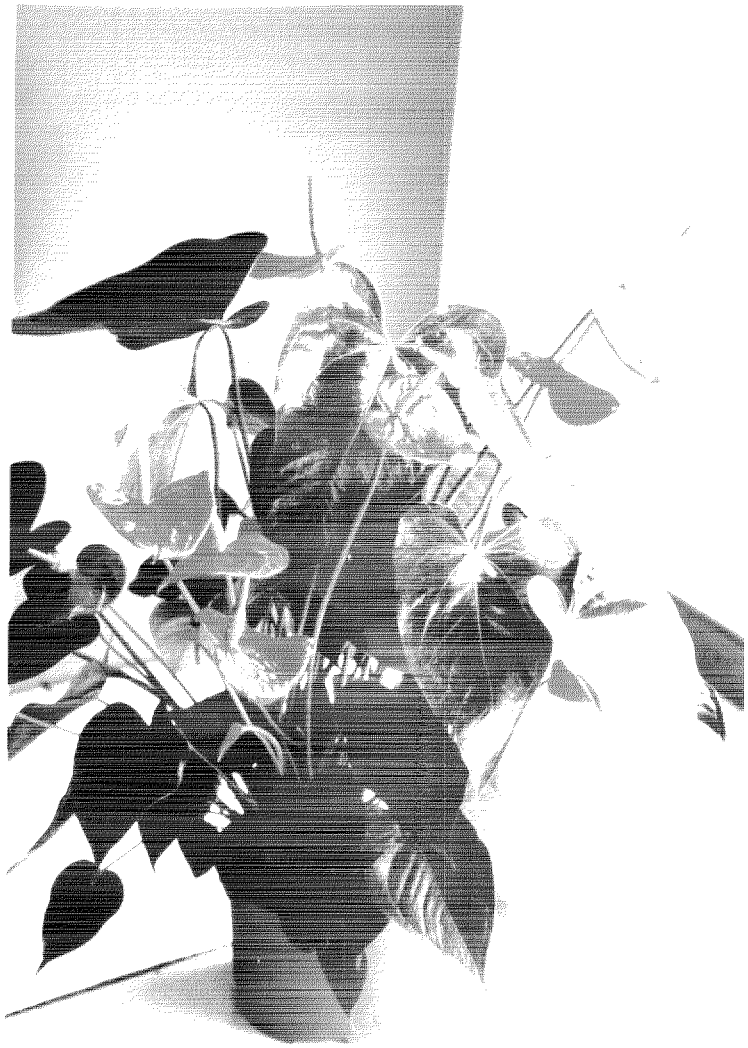

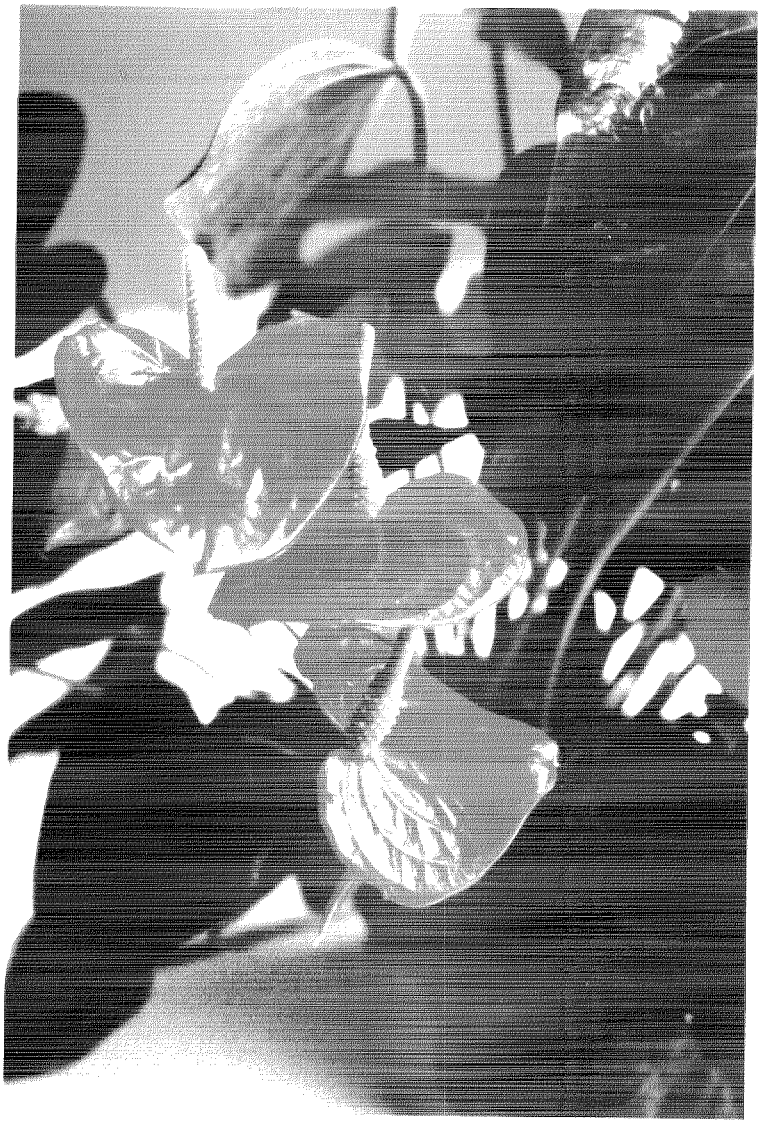

* * * * *